United States Patent
Blackwell et al.

(10) Patent No.: US 11,141,550 B2
(45) Date of Patent: *Oct. 12, 2021

(54) SYSTEMS AND/OR METHODS FOR GUIDING TRANSITIONS BETWEEN THERAPY MODES IN CONNECTION WITH TREATMENT AND/OR DIAGNOSIS OF SLEEP-DISORDERED BREATHING

(71) Applicant: ResMed Pty Ltd, Bella Vista (AU)

(72) Inventors: Andrew Blackwell, Sydney (AU); Gerard Michael O'Connor, Sydney (AU); Marita Elizabeth Barraclough, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 373 days.

This patent is subject to a terminal disclaimer.

(21) Appl. No.: 15/946,514

(22) Filed: Apr. 5, 2018

(65) Prior Publication Data
US 2018/0236192 A1  Aug. 23, 2018

Related U.S. Application Data

(63) Continuation of application No. 15/446,704, filed on Mar. 1, 2017, now abandoned, which is a
(Continued)

(51) Int. Cl.
*A61M 16/00* (2006.01)
(52) U.S. Cl.
CPC ...... *A61M 16/0057* (2013.01); *A61M 16/024* (2017.08); *A61M 2205/3553* (2013.01);
(Continued)

(58) Field of Classification Search
CPC .............. A61M 16/00; A61M 16/0858; A61M 16/0066; A61M 16/0875; A61M 16/0069;
(Continued)

(56) References Cited

U.S. PATENT DOCUMENTS 5,664,562 A  9/1997 Bourdon
5,865,173 A  2/1999 Froehlich
(Continued)

FOREIGN PATENT DOCUMENTS

WO  WO 98/41267 A1  9/1998
WO  WO 02/058619 A2  8/2002
WO  WO 2006/084456 A1  8/2006

OTHER PUBLICATIONS

Feb. 18, 2010 European Search Report issued for European Patent Application No. 09169044.6.
(Continued)

*Primary Examiner* — Jan Christopher L Merene
*Assistant Examiner* — Ned T Heffner
(74) *Attorney, Agent, or Firm* — Nixon & Vanderhye P.C.

(57) ABSTRACT

In certain example embodiments, a system and/or method of guiding transitions between therapy modes in connection with the treatment and/or diagnosis of a patient for a respiratory disorder is/are provided. Respiratory disorder treatment according to a first therapy mode is provided. Input indicating a second therapy mode to be transitioned to following provision of the first therapy mode is received, with the second therapy mode being different from the first therapy mode. At least one default treatment parameter suitable for the second therapy mode is assigned or calculated. Each default treatment parameter of the second therapy mode is presented, with each default treatment parameter being adjustable by an operator during the presenting. Transitioning from the first therapy mode to the second therapy mode is performed by providing respiratory disorder treatment in accordance with the second therapy mode and each default treatment parameter and any adjustments made thereto prior to the transitioning. Advanta-
(Continued)

geously, the chances of a patient being disturbed by transitioning from mode-to-mode are reduced.

38 Claims, 9 Drawing Sheets

Related U.S. Application Data continuation of application No. 12/550,489, filed on Aug. 31, 2009, now Pat. No. 9,586,014.

(60) Provisional application No. 61/193,163, filed on Oct. 31, 2008.

(52) U.S. Cl.
CPC ......... *A61M 2205/3584* (2013.01); *A61M 2205/3592* (2013.01); *A61M 2205/502* (2013.01)

(58) Field of Classification Search
CPC .......... A61M 16/04; A61M 16/0003; A61M 16/105; A61M 16/043; A61M 16/0463; A61M 16/0475; A61M 16/0477; A61M 16/0484; A61M 16/0486; A61M 16/0051; A62B 7/00; A62B 9/006
See application file for complete search history.

(56) References Cited

U.S. PATENT DOCUMENTS

| | | | |
|---|---|---|---|
| 5,970,975 | A | 10/1999 | Estes et al. |
| 6,530,372 | B1 | 3/2003 | Madaus et al. |
| 9,586,014 | B2 * | 3/2017 | Blackwell ........... A61M 16/024 |
| 2005/0166922 | A1 | 8/2005 | Knepper |
| 2006/0162727 | A1 | 7/2006 | Biondi et al. |
| 2007/0017515 | A1 * | 1/2007 | Wallace ............ A61M 16/0051 128/204.23 |
| 2008/0041383 | A1 * | 2/2008 | Matthews ......... A61M 16/0051 128/204.23 |
| 2009/0205663 | A1 | 8/2009 | Vandine et al. |
| 2010/0218766 | A1 | 9/2010 | Milne |
| 2012/0024286 | A1 | 2/2012 | Boring |

OTHER PUBLICATIONS

Apr. 14, 2014 Office Action issued in corresponding European Application No. 09169044.6.

* cited by examiner

Switch CPAP To S,ST,T

| From CPAP | | To S,ST,T | |
|---|---|---|---|
| Pressure: | 7 | Mode: | S |
| EPR Level: | 2 | IPAP: | 7.0 |
| EPR Inhale: | Fast | EPAP: | 5.0 |
| | | Respiratory Rate: | 12 |
| | | Rise Time: | Min |
| | | Ti Max: | 3.0 |
| | | Ti Min: | 0.1 |
| | | Ti: | 0.2 |
| | | Trigger: | Medium |
| | | Cycle: | Medium |

[ OK ]  [ Cancel ]

Fig. 4

Switch CPAP To VAUTO

| From CPAP | | To VAUTO | |
|---|---|---|---|
| Pressure: | 7 | Max IPAP: | 16.0 |
| EPR Level: | 2 | Min EPAP: | 4.0 |
| EPR Inhale: | Fast | PS: | 2.0 |
| | | Ti Max: | 3.0 |
| | | Ti Min: | 0.1 |
| | | Trigger: | Medium |
| | | Cycle: | Medium |
| | | Exhale: | Slow |

[ OK ]  [ Cancel ]

Fig. 5

Switch AutoSet To S,ST,T

| From AutoSet | | To S,ST,T | |
|---|---|---|---|
| Current Pressure: | 4 | Mode: | ST |
| Max Pressure: | 16.0 | IPAP: | 4.0 |
| Min Pressure: | 5 | EPAP: | 4.0 |
| EPR Level: | 2 | Respiratory Rate: | 13 |
| | | Rise Time: | Min |
| | | Ti Max: | 3.0 |
| | | Ti Min: | 0.1 |
| | | Ti: | 0.2 |
| | | Trigger: | Medium |
| | | Cycle: | Medium |

[ OK ]  [ Cancel ]

Fig. 6

Switch AutoSet To VAUTO

| From AutoSet | | To VAUTO | |
|---|---|---|---|
| Current Pressure: | 4 | Max IPAP: | 16.0 |
| Max Pressure: | 16.0 | Min EPAP: | 4.0 |
| Min Pressure: | 5 | PS: | 2.0 |
| EPR Level: | 2 | Ti Max: | 3.0 |
| | | Ti Min: | 0.1 |
| | | Trigger: | Medium |
| | | Cycle: | Medium |
| | | Exhale: | Slow |

[ OK ]  [ Cancel ]

Switch S,ST,T To VAUTO

| From S,ST,T | | To VAUTO | |
|---|---|---|---|
| Mode: | S | Max IPAP: | 20.0 |
| IPAP: | 12.0 | Min EPAP: | 4.0 |
| EPAP: | 8.0 | PS: | 4.0 |
| Respiratory Rate: | 13 | Ti Max: | 3.0 |
| Rise Time: | Min | Ti Min: | 0.1 |
| Ti Max: | 3.0 | Trigger: | Medium |
| Ti Min: | 0.1 | Cycle: | Medium |
| Ti: | 0.2 | Exhale: | Medium |
| Trigger: | Medium | | |
| Cycle: | Medium | | |

[ OK ]   [ Cancel ]

Fig. 9

Switch VAUTO To S,ST,T

| From VAUTO | | To S,ST,T | |
|---|---|---|---|
| Current IPAP: | 8.0 | Mode: | S |
| Current EPAP: | 4.0 | IPAP: | 4.0 |
| Max IPAP: | 20 | EPAP: | 8.0 |
| Min EPAP: | 4.0 | Respiratory Rate: | 13 |
| PS: | 4.0 | Rise Time: | 700 |
| Ti Max: | 3.0 | Ti Max: | 3.0 |
| Ti Min: | 0.1 | Ti Min: | 0.1 |
| Trigger: | Medium | Ti: | 0.2 |
| Cycle: | Medium | Trigger: | Medium |
| Exhale: | Medium | Cycle: | Medium |

[ OK ]   [ Cancel ]

SYSTEMS AND/OR METHODS FOR GUIDING TRANSITIONS BETWEEN THERAPY MODES IN CONNECTION WITH TREATMENT AND/OR DIAGNOSIS OF SLEEP-DISORDERED BREATHING

CROSS-REFERENCE TO RELATED APPLICATION

This application is a continuation of U.S. application Ser. No. 15/446,704, filed Mar. 1, 2017, which is a continuation of U.S. application Ser. No. 12/550,489, filed Aug. 31, 2009, now issued U.S. Pat. No. 9,586,014, which claims the benefit of U.S. Application Ser. No. 61/193,163, filed on Oct. 31, 2008, the entire contents of which are hereby incorporated herein by reference.

FIELD OF THE INVENTION

The example embodiments disclosed herein relate to systems and/or methods for guiding transitions between therapy modes using devices suitable for treating respiratory disorders such as respiratory insufficiency (RI)/failure and/or sleep-disordered breathing (SDB). More particularly, the example embodiments disclosed herein relate to systems and/or methods that enable an operator or sleep clinician to progress through a series of different treatment modes during the diagnosis and titration of a patient for RI, SDB, or the like. When transitioning between first and second treatment modes having at least one different treatment parameter (either definitionally, by virtue of an operator or sleep clinician entering a particular value for a parameter of the second mode that differs from a corresponding value of the first mode, etc.), potential disruptions to the patient are reduced by reducing (and sometimes even eliminating) potentially large or unpleasant pressure transitions.

BACKGROUND OF THE INVENTION

Obstructive Sleep Apnea (OSA) and other dangerous sleep-disordered breathing (SDB) conditions affect thousands worldwide. Numerous techniques have emerged for treating SDB, including, for example, the use of Positive Airway Pressure (PAP) devices, which continuously provide pressurized air or other breathable gas to the entrance of a patient's airways via a patient interface (e.g. a mask) at a pressure elevated above atmospheric pressure, typically in the range 3-20 cm $H_2O$. Typically, patients suspected of suffering from SDB register with a certified sleep laboratory where sleep technicians fit patients with numerous data collectors and monitor their sleep activity over a given period. After the patient is diagnosed, a treatment regimen usually is developed, identifying both a treatment apparatus (or treatment apparatuses) and program of use for the treatment apparatus(es).

FIG. 1 shows a simplified schematic of a typical CPAP treatment apparatus. An impeller 1 is powered by an electric motor 2 using a servo 3 under the direction of a microprocessor-based controller 4. The supply of breathable gas is carried to the mask 5 through a flexible conduit 6. The apparatus has various switches 7, displays 8, and a number of transducers. The transducers may monitor a number of processes, such as, for example volumetric flow rate 10 (e.g., at a predetermined point in the flow path), pressure 11 (e.g., at a predetermined point downstream of the flow generator outlet or at the mask), snore 12, flow generator rotational speed 13, and/or motor parameters 14.

It is well known for sleep clinics to observe and treat patients with respiratory disorders such as SDB or respiratory insufficiency (RI) with devices like the one shown in FIG. 1. Observable symptoms of SDB and/or RI only occur during sleep. Thus, it will be appreciated that disturbing a sleeping patient wastes effort and resources, and also reduces the amount of effective time that may be used to titrate the patient for an optimal therapeutic result. Accordingly, care must be taken when diagnosing and/or administering treatment to a patient, e.g., so as not to wake up the patient.

SDB symptoms often are layered. That is, treating one symptom may reveal yet another. Thus, the complicated nature of SDB symptoms typically means that a sleep clinician will attempt various different PAP therapies when diagnosing and/or treating a patient. As is known, each PAP therapy has a unique combination of settings that must be controlled. Unfortunately, it often is difficult to systematically and methodically attempt various PAP therapies and, similarly, it also is difficult to systematically and methodically vary the particular settings of a particular PAP therapy. Furthermore, switching from one PAP therapy mode to another may involve possibly large changes to one or more treatment parameters that may cause problems for the patient and/or cause the patient to wake up during diagnosis and/or treatment, thus leading to the above-noted disadvantages.

Thus, it will be appreciated that there is a need in the art for systems and/or methods that make it easier for a sleep clinician to diagnose and/or administer a treatment.

SUMMARY OF THE INVENTION

One aspect of certain example embodiments relates to systems and/or methods that make it easier for an operator or sleep clinician to diagnose and/or titrate a respiratory disorder treatment therapy by facilitating the systematic and/or methodical transition of settings within a particular treatment mode, and/or by facilitating the systematic and/or methodical transition between first and second treatment modes.

Another aspect of certain example embodiments relates to systems and/or methods for reducing the differences perceivable by a patient when treatment and/or titration modes are changed.

Still another aspect of certain example embodiments relates to presenting an operator or sleep clinician with a menu or list of adjustable treatment parameters for a new therapy mode to be transitioned to, prior to any transitioning from a current therapy mode to the new therapy mode. Optionally, the treatment parameters displayed in the menu or list may be values recommended to the operator or sleep clinician (e.g., based on best practice guidelines, current treatment parameters, assignments or calculations regarding current and expected effectiveness of various treatments, etc.).

Still another aspect of certain example embodiments relates to adjusting one or more treatment parameters from a first level through at least one intermediate level and ultimately to a second level during a transition period in which treatment is changed from a first treatment mode to a second treatment mode.

Advantageously, the techniques of certain example embodiments simplify the transition of one therapy to another increases operator confidence. Furthermore, recommending settings for the new therapy advantageously enables best practice guidelines to be implemented, e.g., without restricting operator control and while also reducing the likelihood of disturbing a sleeping patient as a result of the transition.

In certain example embodiments of this invention, a method of guiding transitions between therapy modes in connection with the treatment and/or diagnosis of a patient for a respiratory disorder is provided. Respiratory disorder treatment is provided according to a first therapy mode. Input indicating a second therapy mode to be transitioned to following provision of the first therapy mode is received, with the second therapy mode being different from the first therapy mode. At least one default treatment parameter suitable for the second therapy mode is assigned or calculated. Each said default treatment parameter of the second therapy mode is presented, and each said default treatment parameter is adjustable by an operator during said presentation. Transitioning from the first therapy mode to the second therapy mode is performed by providing respiratory disorder treatment in accordance with the second therapy mode and each said default treatment parameter and any adjustments made thereto prior to said transitioning.

In certain example embodiments, a system for guiding transitions between therapy modes provided to a patient suffering from a respiratory disorder is provided. A flow generator is configured to supply a plurality of therapy modes to the patient. The flow generator is further configured to: (1) receive input indicating a second therapy mode to be transitioned to following provision of a first therapy mode, with said second therapy mode being different from said first therapy mode; and (2) transition from the first therapy mode to the second therapy mode in accordance with instructions as to how to perform the transition, with the instructions being indicative of at least one default treatment parameter suitable for the second therapy mode and any changes made by an operator to each said default treatment parameter prior to the transition.

In certain example embodiments, a flow generator configured to supply a plurality of therapy modes to a patient suffering from a respiratory disorder is provided. An input mechanism is configured to receive input indicating a second therapy mode to be transitioned to following provision of a first therapy mode, with the second therapy mode being different from said first therapy mode. A processor is configured to guide the transition from the first therapy mode to the second therapy mode by transitioning from the first therapy mode to the second therapy mode in accordance with instructions as to how to perform the transition, with the instructions being indicative of at least one default treatment parameter suitable for the second therapy mode and any changes made by an operator to each said default treatment parameter prior to the transition.

In certain example embodiments, a computer-readable storage medium tangibly storing a program for guiding transitions between therapy modes in connection with the treatment and/or diagnosis of a patient for a respiratory disorder is provided. The program causes a flow generator to perform a method comprising providing respiratory disorder treatment according to a first therapy mode; receiving information concerning at least one default treatment parameter suitable for a second therapy mode to be transitioned to, the second therapy mode being different from the first therapy mode; and transitioning from the first therapy mode to the second therapy mode by providing respiratory disorder treatment in accordance with the second therapy mode and each said default treatment parameter and any adjustments made thereto prior to said transitioning.

BRIEF DESCRIPTION OF THE DRAWINGS

The accompanying drawings facilitate an understanding of the various embodiments of this invention. In such drawings:

FIG. 4 is an illustrative control screen for controlling a transition from CPAP to S/ST/T therapy in accordance with an example embodiment;

FIG. 5 is an illustrative control screen for controlling a transition from CPAP to VAUTO therapy in accordance with an example embodiment;

FIG. 6 is an illustrative control screen for controlling a transition from AutoSet to S/ST/T therapy in accordance with an example embodiment;

FIG. 7 is an illustrative control screen for controlling a transition from AutoSet to VAUTO therapy in accordance with an example embodiment;

FIG. 8 is an illustrative control screen for controlling a transition from S/ST/T to VAUTO therapy in accordance with an example embodiment;

FIG. 9 is an illustrative control screen for controlling a transition from VAUTO to S/ST/T therapy in accordance with an example embodiment.

DETAILED DESCRIPTION OF ILLUSTRATED EMBODIMENTS

1. Introduction

Figure 1:
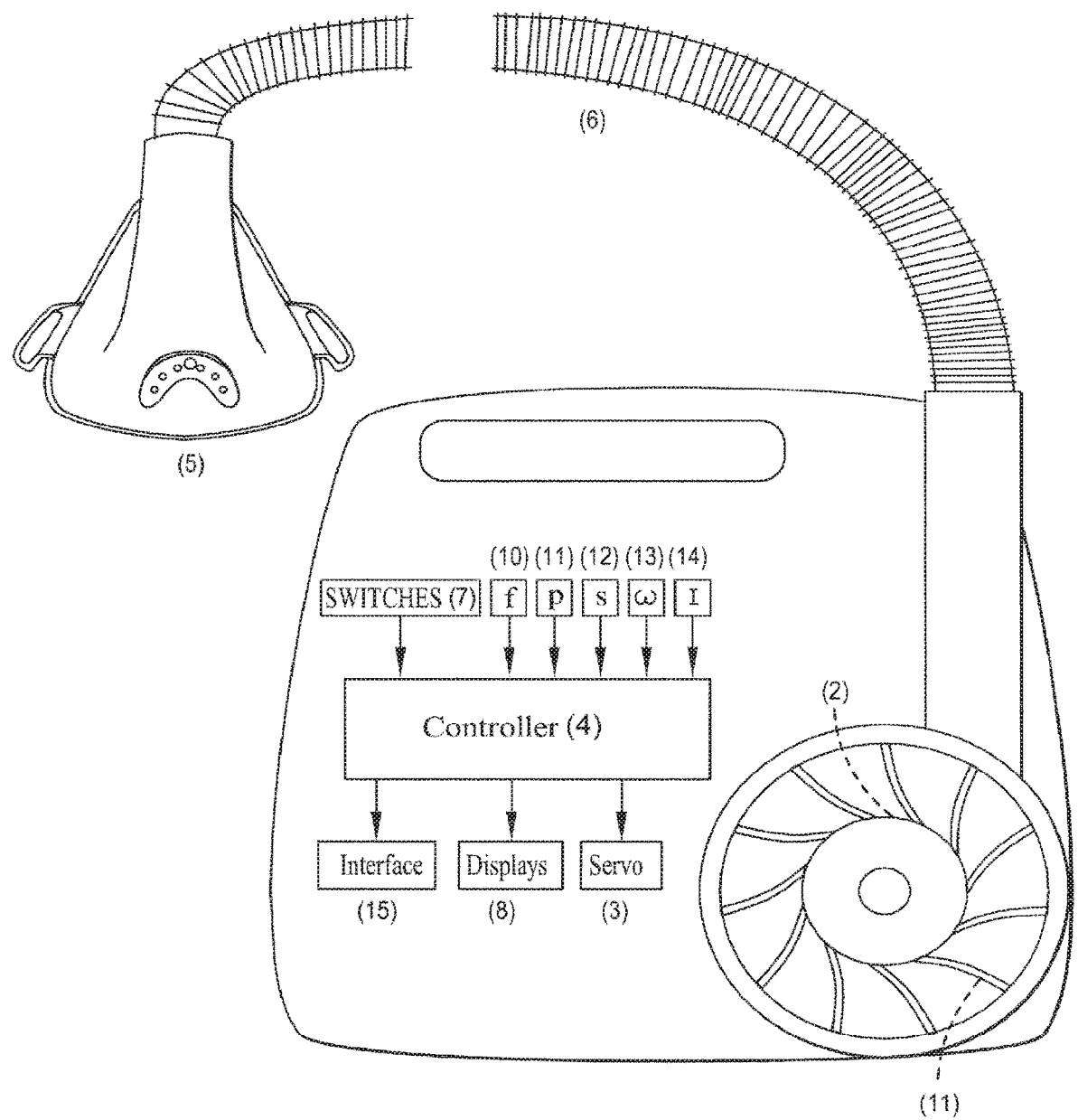
FIG. 1 shows a simplified schematic of a typical CPAP treatment apparatus.

Certain example embodiments of this invention relate to systems and/or methods that make it easier for an operator or sleep clinician to diagnose and/or titrate a treatment therapy by facilitating the systematic and/or methodical transition of settings within a particular treatment mode, and/or by facilitating the systematic and/or methodical transition between first and second treatment modes. Indeed, certain example embodiments relate to systems and/or methods for reducing the differences perceivable by a patient when treatment modes are changed. This may be accomplished by presenting an operator or sleep clinician with a menu or list of adjustable treatment parameters for a new therapy mode to be transitioned to, prior to any transitioning from a current therapy mode to the new therapy mode. In certain example embodiments, the treatment parameters displayed in the menu or list may be recommended to the operator or sleep clinician (e.g., based on best practice guidelines, current treatment parameters, calculations regarding current and expected effectiveness of various treatments, etc.). In certain example embodiments, one or more treatment parameters may be adjusted from a first level through at least one intermediate level and ultimately to a second level during a transition period in which treatment is changed from a first treatment mode to a second treatment mode.

Advantageously, the techniques of certain example embodiments simplify the transition of one therapy to another and increase operator confidence. Furthermore, recommending settings for the new therapy advantageously enables best practice guidelines to be implemented, e.g., without restricting operator control and while also reducing the likelihood of disturbing a sleeping patient as a result of the transition.

In general, these features are enabled by (1) providing an application tangibly stored on a computer-readable storage medium for titration control that incorporates features for managing therapy transitions, and/or (2) providing a remotely controllable flow generator incorporating multiple therapies in a single device, wherein all therapy settings are fully accessible at all times. Example details regarding the same are provided in the sections that follow.

2. Example Progressions and Transitions

This section notes that certain example embodiments may progress from therapy mode to therapy mode and provides illustrative, non-limiting examples of such therapy modes. In other words, this section lists a number of exemplary therapy modes, along with an indication of the types of transitions that may be permitted in accordance with certain example embodiments. It also provides several illustrative, non-limiting examples of how changes may be made when transitioning from one mode to another.

2.1 Example Progression From Therapy Mode to Therapy Mode

A variety of progressions of therapies may be supported. In certain example embodiments, the therapies supported may include, for example, CPAP, AutoSet, VAUTO, and S/ST/T therapies. Briefly, CPAP therapy involves providing continuous positive airway pressure at a pressure level (e.g., which may be fixed) above atmospheric. AutoSet therapy involves the automatic titration or tuning of the amount of pressure delivered to the patient to the minimum required to maintain an unobstructed airway on a breath-by-breath basis, e.g., by measuring the resistance in the patient's breathing, thereby giving the patient the precise pressure required at a given moment and avoiding the compromise of fixed pressure. VPAP (or BiLevel) therapy provides two levels of pressure—namely, a first level of pressure for Inspiratory Positive Airway Pressure (IPAP), and a second level of pressure for Expiratory Positive Airway Pressure (EPAP) for easier exhalation. VAUTO therapy is an auto-adjusting BiLevel therapy mode. As noted above, an operator or sleep clinician may make such changes to try to find the optimal treatment for a patient, to discover and subsequently define a treatment regimen for "layered" SDB symptoms, etc. A typical example of layered symptoms involves the use of CPAP therapy to effectively treat obstructive sleep apnea, only to discover that the patient also suffers nocturnal hypoventilation and requires a bi-level therapy that can offer respiratory support, such as VAUTO, or S/ST. Similarly, after treating obstructive sleep apnea, central sleep apnea events may be observed in the patient. At this point the patient would require treatment with adaptive support ventilation (or ASV, which is described in greater detail below) therapy. Furthermore, as described in greater detail below, a recommendation may be generated (e.g., by the application and/or flow generator of certain example embodiments) to prompt the user to switch modes. The recommendation may be based on judgments performed by the application and/or flow generator of certain example embodiments, which may interpret received treatment and patient response data in light of preprogrammed, optionally updateable, rules (which may be based on current best practice guidelines, for example). Based on such a judgment, the user may be presented with the recommendation and asked to confirm a change in therapy modes, the flow generator may transition automatically without direct user input, etc. In certain example embodiments, the application or flow generator of certain example embodiments may monitor one or more parameters (e.g., snoring sound, lack of breathing effort, progressiveness of increased apneas, etc.), and provide a recommendation to an operator or clinician to make a change to another therapy. In certain example embodiments, based on such information, the application or flow generator of certain example embodiments may suggest the particular therapy to be transitioned to.

S/ST/T therapies involve differing techniques for triggering IPAP. For example, in S (Spontaneous) mode, the device triggers IPAP when flow sensors detect spontaneous inspiratory effort and then cycles back to EPAP, whereas the IPAP/EPAP cycling is purely machine-triggered (e.g., at a set rate, typically expressed in breaths per minute (BPM)) in T (Timed) mode. In ST (Spontaneous/Timed) mode, like S mode, the device triggers to IPAP on patient inspiratory effort, although a "backup" rate also is set to ensure that a patient still receives a minimum number of breaths per minute if the patient fails to breathe spontaneously. In other words, ST therapy allows the patient to breathe at the patient's normal respiratory rate and, if the patient experiences an apnea or falls below the set rate, the device supports the patient's ventilation with a timed breath.

ASV therapy is a positive pressure mode of mechanical ventilation that is closed-loop controlled, in which the frequency and tidal volume of breaths of a patient on the ventilator are automatically adjusted based on the patient's requirements. For example, lung mechanics data are used to adjust the depth and rate of breaths to reduce the work rate of breathing. Every breath is synchronized with patient effort if such an effort exists, otherwise, full mechanical ventilation is provided to the patient.

Figure 2:
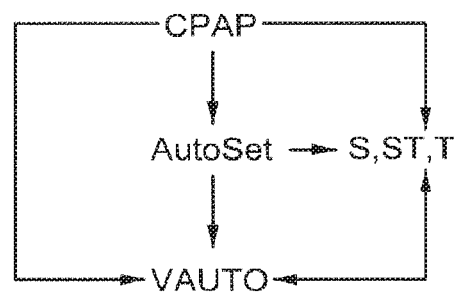
FIG. 2 is an example progression of therapies that may be used in connection with certain example embodiments.

Of course, it will be appreciated that different embodiments of this invention may incorporate some, all, none, or different therapy modes. FIG. 2 is an example progression of therapies that may be used in connection with certain example embodiments. As shown in FIG. 2, CPAP therapy may transition to either AutoSet, VAUTO, or S/ST/T therapy. AutoSet therapy, in this example, may transition to VAUTO or S/ST/T therapy. Finally, in this example, AutoSet and S/ST/T therapies may transition only to one another.

It will be appreciated that other combinations of "to" and "from" modes may be provided in connection with certain example embodiments. Furthermore, even in connection with the example transitions shown in FIG. 2, it will be appreciated that certain example embodiments may enable an operator or sleep clinician to revert to a prior mode or essentially "undo" a transition. For example, a patient may respond fairly well to CPAP therapy mode, and an operator or sleep clinician may want to try applying a VPAP (or BiLevel) therapy mode. If the patient does not respond well to the VPAP (or BiLevel) therapy mode or if the operator or sleep clinician accidentally caused the transition to be made, the operator or sleep clinician may effectively "undo" the transition and "return" to the CPAP therapy mode, e.g., to adjust the parameters of this therapy mode, or to attempt a transition to another therapy mode (such as the AutoSet therapy mode, for example). In certain example embodiments, the modes may be switched only after the transition is complete. However, an operator or sleep clinician alternatively or additionally may interrupt a transition in certain example embodiments. It will be appreciated that the example techniques described herein also may be applied during an "undo" or "reversion" process, such that, for example, the transitioning techniques may help adjust the various treatment parameters during such processes so as to also reduce the likelihood of disturbing a patient during at such times.

3.2 Example Changes Made when Transitioning Between Therapy Modes

Figure 10A:
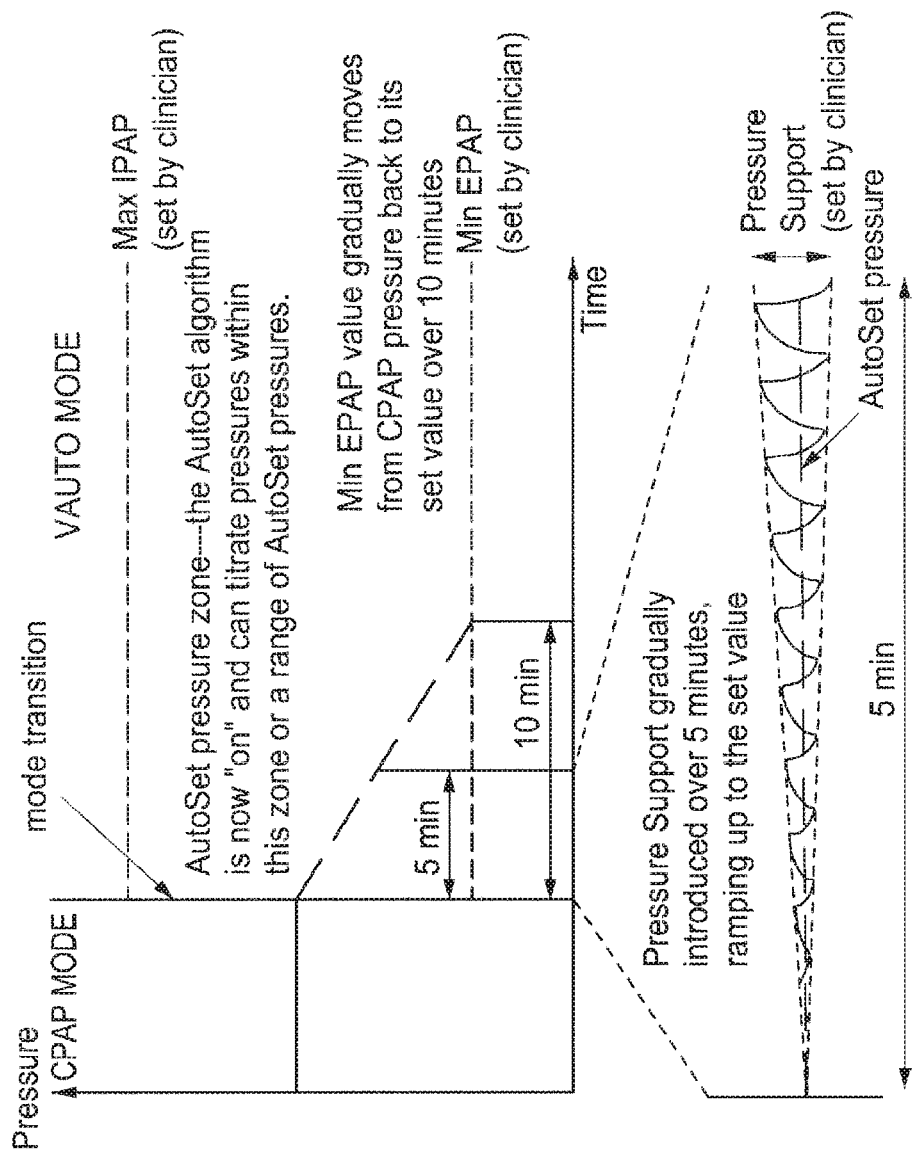
FIG. 10a is a graph illustrating example changes made when transitioning from CPAP therapy mode to VAUTO therapy mode, in accordance with an example embodiment.
Figure 10B:
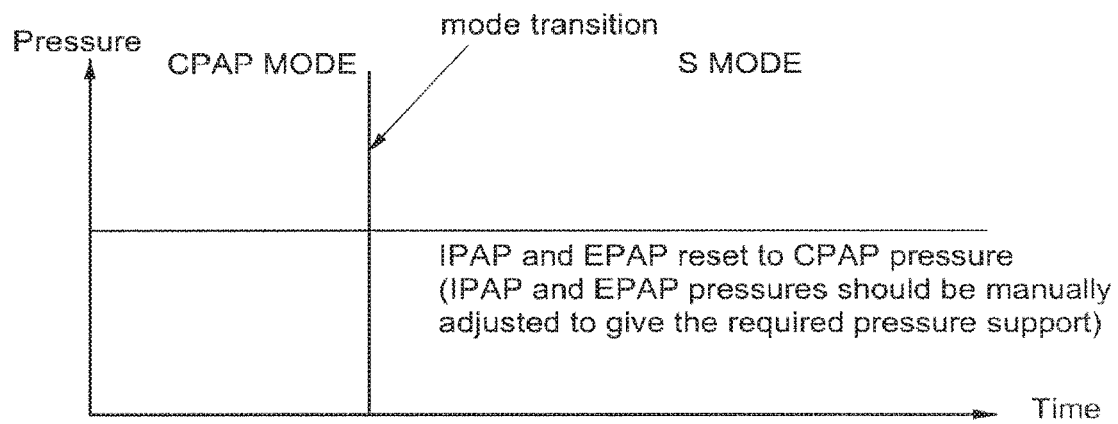
FIG. 10b is a graph illustrating example changes made when transitioning from CPAP therapy mode to S therapy mode, in accordance with an example embodiment.
Figure 10C:
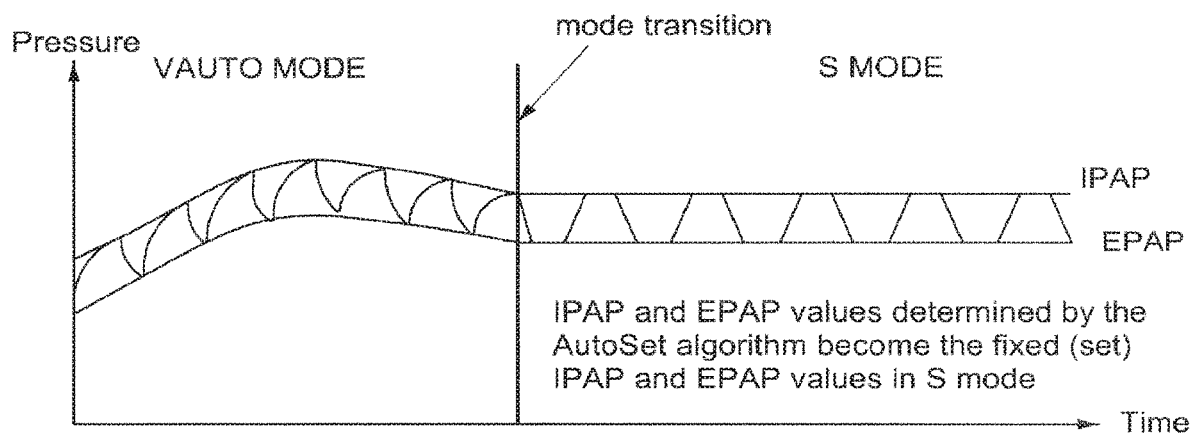
FIG. 10c is a graph illustrating example changes made when transitioning from VAUTO therapy mode to S therapy mode, in accordance with an example embodiment.

FIGS. 10a through 10c visually depict some example changes made when changing between first and second different therapy modes. It will be appreciated that the example changes made when transitioning between therapy modes described below take effect after an operator or clinician is presented with a menu or list of treatment parameters for the mode being transitioned to (e.g., as shown in and described in connection with, for example, FIGS. 2-9) and has confirmed that the treatment parameters for the mode being transitioned to are acceptable (e.g., by pushing the "OK" button in such figures after making any necessary adjustments).

Certain example embodiments allow more supervision and flexibility for the operator or clinician, in that the certain example embodiments recommend how the different parameters are changed without simply making preprogrammed or default changes automatically. Thus, an operator or clinician can review and change the parameters, e.g., at one time and in one step. The actual transition from one mode to another may occur after the operator or clinician has reviewed the parameter recommendations and accepted them (e.g., the operator may be required to take a positive action such as clicking a button to initiate the transition). Thus, the transition to desired parameters occurs in a single step in certain example embodiments, e.g., without the need to touch the flow generator or any components within the room and also in a manner less likely to disturb or otherwise bother the patient. Moreover, in certain example embodiments, each parameter does not necessarily have to be adjusted separately; rather, the parameters all may be adjusted on one screen at one time and then confirmed, such that transition occurs in a single step. The therapy mode change then may be applied (e.g., instantaneously or at the end of the breath to provide the least disruption to the patient). This transition may occur with or without going through an intermediate level, as discussed herein. Also, the system functional control of the guided transitions may be operated on a separate computer, the program also may be stored on a readable memory and/or within the PAP device in certain example embodiments.

More particularly, FIG. 10a is a graph illustrating example changes made when transitioning from CPAP therapy mode to VAUTO therapy mode, in accordance with an example embodiment. When changing from CPAP therapy mode to VAUTO therapy mode, the Min EPAP value may temporarily become the same as the CPAP pressure setting. The Min EPAP value may increase or decrease as required to gradually return to its previously set value over a predetermined time period (e.g., 10 minutes, as shown in FIG. 10a, although other time periods are possible). If the CPAP pressure is greater than the Max IPAP setting, then the starting Min EPAP value may take on the previous Max IPAP pressure setting. On the pressure transition, pressure support may rise from an initial value of zero up to the pressure support setting over a second predetermined time period (e.g., 5 minutes as shown in FIG. 10a).

Apart from, or in addition to the above-described technique, certain example embodiments may transition to an AutoSet therapy mode from a CPAP mode by initializing or "seeding" the AutoSet algorithm to achieve a starting pressure that is equivalent or at least similar to the previous CPAP therapy pressure. In other words, the AutoSet value may be initialized with the CPAP pressure as a "seed" value, and the AutoSet algorithm may begin titrating around the seed value to provide EPAP and IPAP pressures. As will be appreciated from this description, a seed is a value (or set of values) that is used to start a process at a defined initial condition. Maximum and/or minimum EPAP and/or IPAP pressures may be specified in certain example embodiments.

FIG. 10b is a graph illustrating example changes made when transitioning from CPAP therapy mode to S therapy mode, in accordance with an example embodiment. When changing from CPAP therapy mode to S therapy mode, the CPAP pressure setting automatically may transfer as IPAP and EPAP pressure settings in certain example embodiments, such as the one shown visually in FIG. 10b. Alternatively, in certain example embodiments, IPAP and EPAP pressure settings may be defined prior to the transition. In such a case, substantially continuous increases or decreases over a predetermined period of time or number of breaths (e.g., similar to ramping) may help ease the transition from CPAP therapy mode to S therapy mode.

FIG. 10c is a graph illustrating example changes made when transitioning from VAUTO therapy mode to S therapy mode, in accordance with an example embodiment. In such a case, IPAP and EPAP pressures determined by the AutoSet algorithm used for the VAUTO therapy mode may transfer across to become the fixed IPAP and EPAP settings in the S therapy mode. In certain example embodiments, the most recent IPAP and EPAP settings may be used, whereas in certain example embodiments, average IPAP and EPAP settings (taken, for example, over a predetermined amount of time or number of breaths) may be used instead. In the former case, little transitioning is required. However, in the latter case, substantially continuous increases or decreases over a predetermined period of time or number of breaths (e.g., similar to ramping) may help ease the transition from VAUTO therapy mode to S therapy mode, e.g., where there is a large difference between the current IPAP and EPAP settings and the average IPAP and EPAP settings being transitioned to.

It will be appreciated that more transition points and concomitant intermediate levels may be included in connection with certain example embodiments. It also will be appreciated that such intermediate levels may be discrete steps, or may be levels that are gradually substantially continuously built up or throttled down to, similar (though not exactly the same as) conventional "ramping" that is known to be performed when a patient initiates a sleep session. Still further, it will be appreciated that when a particular treatment parameter of a first mode does not have a corresponding treatment parameter in the second mode, or vice versa, transitions may be considered to have been made from this "zero" or "null" condition. Transitions from the zero or null condition may be discrete on/off transitions, or also may pass through intermediate values when progressing from or to the zero or null level.

Although certain particular time periods have been described above, it will be appreciated that other time periods may be used in connection with certain example embodiments. Additionally, it will be appreciated that the transitioning may be breath-based rather than time-based. In other words, instead of a transition occurring over a predetermined amount of time, a transition may occur over a predetermined number of breaths.

3. Example Application for Guiding Transitions

As noted above, certain example embodiments relate to an application tangibly stored on a computer-readable storage medium for titration control that incorporates features for managing therapy transitions. The application of certain example embodiments enables the user to maintain complete control over the therapy transition, for example, by allowing review of current settings, recommending initial settings for the new therapy, enabling adjustment of settings for the new therapy, performing therapy transition in a single transaction, and/or the like.

FIGS. 3-9 are illustrative control screens for managing therapy transitions in accordance with an example embodiment, each of which will be described in greater detail below. Of course, it will be appreciated that different control screens may be used in connection with different embodiments of this invention. For example, the control screens may include different interface features (e.g., text boxes, selection lists, drop boxes, increment/decrement counters, etc.); some, all, none or alternative treatment parameters may be included, changeable, and/or fixed; etc. In general, FIGS. 3-9 show the "from" mode on the left-hand side of the illustrative screen, and the "to" mode on the right-hand side of the illustrative. However, the present invention is not limited to this configuration.

Additionally, the application that displays illustrative control screens may be provided on the PAP device, or it may be in wired or wireless connection with the PAP device. For example, the application may be executable on a computer located remote from the PAP device, e.g., such that an operator or sleep clinician can use the application from a distance and/or location less likely to interfere with the patient's sleep.

These illustrative screens may be presented to an operator or clinician prior to a transition taking place in certain example embodiments. Indeed, an operator or clinician may adjust the treatment parameters via appropriate interfaces to help reduce unsettling effects that a patient might experience when the transition is made. Titration in accordance with the particular mode being transitioned to may occur after the transition is made. That is, in accordance with certain example embodiments, a first therapy mode may be provided, an operator or clinician may be presented with a menu or list of adjustable treatment parameters for a second mode to be transitioned to (which menu or list may be prepopulated in accordance with recommendations based on, for example, best practice guidelines, assigned or calculated parameters, etc.), a second therapy mode may be provided in accordance with the specified treatment parameters for at least a predetermined amount of time or number of breaths, and then titration in accordance with the second therapy mode may be provided.

Figure 3:
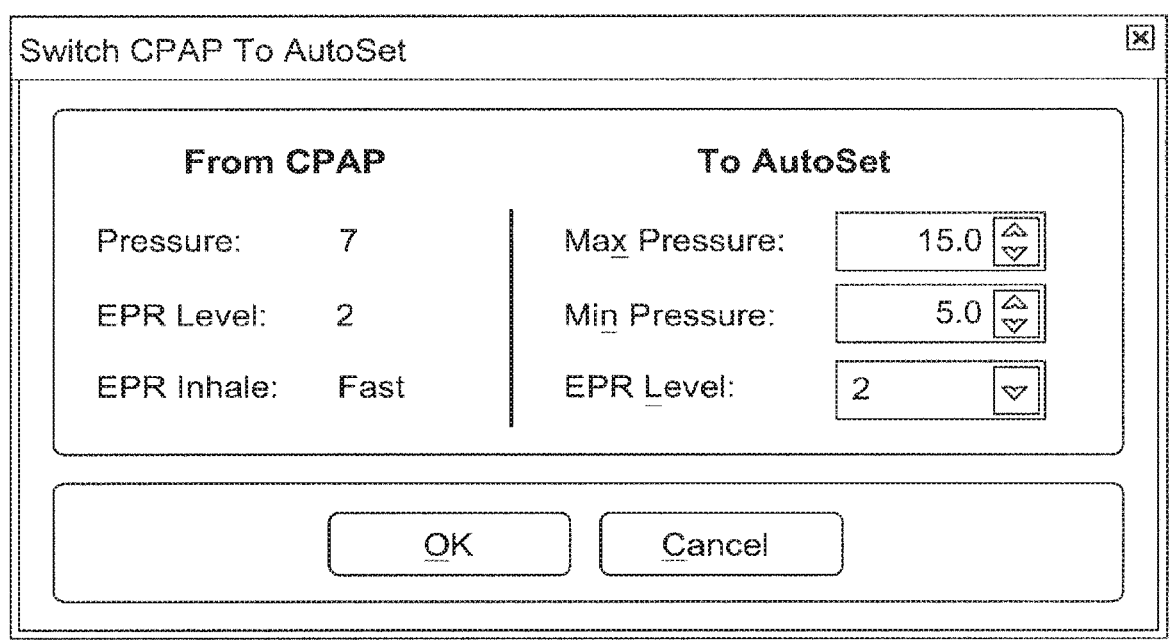
FIG. 3 is an illustrative control screen for controlling a transition from CPAP to AutoSet therapy in accordance with an example embodiment.

FIG. 3 is an illustrative control screen for controlling a transition from CPAP to AutoSet therapy in accordance with an example embodiment. The left-hand side of the illustrative screen shows the status of current treatment parameters including, for example, pressure (e.g., in cm $H_2O$), Expiratory Pressure Release (EPR) level, and EPR Inhale speed. The right-hand side of the illustrative screen shows adjustable treatment parameters for the mode to be transitioned to which, in this example, is the AutoSet mode. The treatment parameters include, for example, maximum and minimum pressures (e.g., in cm $H_2O$), and EPR level.

Here, as elsewhere, the treatment parameters for the mode to be transitioned to may automatically default to recommended settings, e.g., appropriate for the particular therapy mode about to be delivered. Recommended settings may be pre-programmed in the application, accessible from a computer-readable storage medium connected to the application (e.g., via a disk, CD-ROM, flash drive, network connection, etc.), etc. Thus, recommended settings may be set to current best practice levels and may be subsequently adjusted based on, for example, forthcoming research, further discoveries, operator or sleep clinician intuitions or preferences, prior patient experience, etc. The same and/or similar functionality also may apply to other illustrative display screens.

FIG. 4 is an illustrative control screen for controlling a transition from CPAP to S/ST/T therapy in accordance with an example embodiment. The current treatment parameters for CPAP therapy have been described above and may thus be the same as those noted above. The right-hand side of the illustrative screen shows adjustable treatment parameters for the mode to be transitioned to which, in this example, is the S/ST/T therapy mode. The treatment parameters include, for example, the particular sub-mode (e.g., S, ST, or T), IPAP and EPAP (e.g., in cm $H_2O$), respiratory rate (e.g., in breaths per minute), rise time (e.g., a discrete or absolute time between when the pressure ramps up from EPAP to IPAP), maximum time spent in IPAP (or Ti max), minimum time spent in IPAP (or Ti min), absolute time spent in IPAP (or Ti), the level of inspiratory flow above which EPAP transitions to IPAP or Trigger (e.g., as expressed discretely or as an absolute pressure level), the level of inspiratory flow below which IPAP transitions to EPAP or Cycle (e.g., as expressed discretely or as an absolute pressure level), etc. As shown in FIG. 4, the operator or sleep clinician may specify the S, ST, or T "sub-therapy" using a drop-down box. However, the present invention is not limited to this arrangement. For example, a series of radio or other buttons may be provided, separate screens may be provided for each of the sub-therapy modes, etc.

It will be appreciated that the treatment parameters may be selectively enabled or disabled based, in part, on the particular sub-mode, etc. For example, Ti Max and Ti Min may be enabled and Ti may be disabled when S mode is selected, whereas all there may be enabled when ST mode is selected. The same and/or similar functionality also may apply to other illustrative display screens.

FIG. 5 is an illustrative control screen for controlling a transition from CPAP to VAUTO therapy in accordance with an example embodiment. The current treatment parameters for CPAP therapy have been described above and may thus be the same as those noted above. The right-hand side of the illustrative screen shows adjustable treatment parameters for the mode to be transitioned to which, in this example, is the VAUTO therapy mode. The treatment parameters include, for example, maximum IPAP pressure (e.g., in cm $H_2O$), minimum EPAP pressure (e.g., in cm $H_2O$), pressure support or PS setting (e.g., the difference between IPAP and EPAP, e.g., in cm $H_2O$), maximum time spent in IPAP (or Ti max), minimum time spent in IPAP (or Ti min), transitions to IPAP or Trigger (e.g., as expressed discretely or as an absolute pressure level), the level of inspiratory flow below which IPAP transitions to EPAP or Cycle (e.g., as expressed discretely or as an absolute pressure level), exhale time (e.g., as a discrete value such as fast, medium, slow, etc.), etc.

FIG. 6 is an illustrative control screen for controlling a transition from AutoSet to S/ST/T therapy in accordance with an example embodiment. FIG. 7 is an illustrative control screen for controlling a transition from AutoSet to VAUTO therapy in accordance with an example embodiment. FIG. 8 is an illustrative control screen for controlling a transition from S/ST/T to VAUTO therapy in accordance with an example embodiment. FIG. 9 is an illustrative control screen for controlling a transition from VAUTO to S/ST/T therapy in accordance with an example embodiment. Example treatment parameters for each of the above-noted modes have been described above. The same or similar treatment parameters may be shown and/or adjustable, where appropriate, as will be apparent to those skilled in the art. Thus, further discussion of these figures will be omitted.

In certain example embodiments, once an operator or sleep clinician has indicated the new therapy mode to be transitioned to, the PAP device may automatically transition from the current therapy mode to the new therapy mode. Such transitioning may be facilitated by the adjustment therapy parameters from initial levels through one or more respective intermediate level(s) and ultimately to the new levels, e.g., based on predefined criteria. For example, a PAP device may be configured to gradually ramp up pressure in a substantially continuous manner from a first level to a second level, or in a more stepwise fashion (e.g., from a low level through an intermediate level to a high level). It will be appreciated that the transitioning from first levels through intermediate levels to second levels need not necessarily take place for all treatment parameters. For example, when transitioning from CPAP therapy to AutoSet therapy, the target pressure may be increased substantially continuously whereas the EPR level may jump directly from a first value to a second value. In general, the predefined criteria may guide the transition from mode-to-mode and automatically provide the individual treatment parameter changes.

In certain example embodiments, however, an operator or sleep clinician may indicate with more specificity how the transitions are to be made from mode-to-mode. In this regard, in certain example embodiments, an operator or sleep clinician may be presented with an interface that allows the operator or sleep clinician to indicate, for example, how specific treatment parameters are to be adjusted (e.g., discretely, substantially continuously, through one or more preset or automatically defined intermediate levels, etc.). In certain example embodiments, the user interface may provide default recommended transitions, e.g., so as to guide the transitions according to best practices. As above, the recommendations may be predefined to reflect current best practices and/or may be updateable, e.g., in dependence on forthcoming research, further discoveries, operator or sleep clinician intuitions or preferences, prior patient experience, etc.

4. Example Systems for Guiding Transitions

As noted above, certain example embodiments relate to a remotely controllable flow generator incorporating multiple therapies in a single device, wherein all therapy settings are fully accessible at all times. In this regard, the flow generator of certain example embodiments may support the therapy transition as a single transaction timed towards the end of the patient's breath cycle or near the end of patient expiration. For automated therapies, the flow generator may further support transition by seeding the automation logic with the correct initial conditions.

In general, the application and/or systems of certain example embodiments may guide the operator or sleep clinician through a sequence or series of therapies, e.g., in accordance with a predetermined recommended best plan that, again, may be updateable. During the treatments, based on patient response, for example, the user interfaces may display and/or process the data, thus allowing the treatment to be adjusted in accordance with the efficacy of the treatment, either automatically, upon receipt of signals from the operator or sleep clinician, or under a combination of the two (e.g., where a recommendation is made automatically and subsequently confirmed by the operator or sleep clinician, where transitions automatically occur if not acted upon within a predetermined amount of time, etc.), and/or the like.

Figure 11:
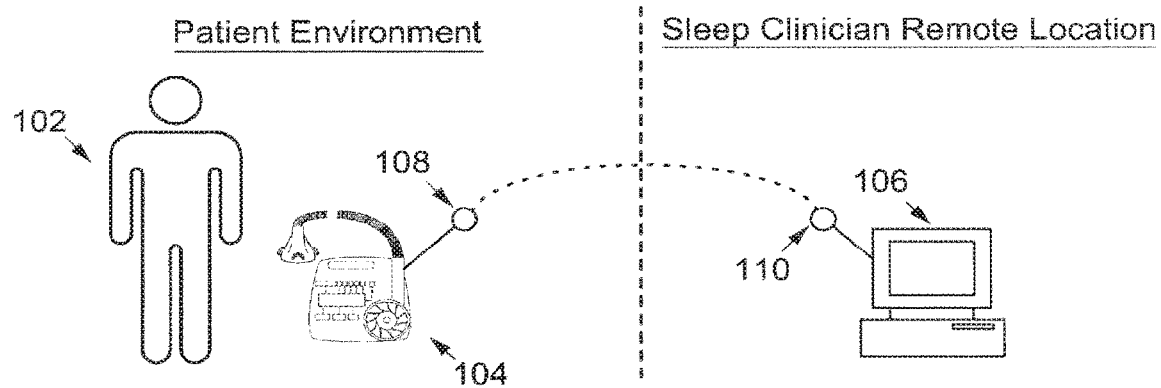
FIG. 11 is an example system for guiding transitions between therapy modes during the course of SDB treatment and/or diagnosis, in accordance with an example embodiment.

FIG. 11 is an example system for guiding transitions between therapy modes during the course of SDB treatment and/or diagnosis, in accordance with an example embodiment. A patient 102 is connected to a flow generator 104 according to an example embodiment in a patient environment. An operator or sleep clinician may be located at a location remote from the patient environment. From this remote location, the operator or sleep clinician may monitor the progress of the diagnosis and/or treatment of the patient 102 using the computer terminal 106 which, in certain example embodiments, may be running the example application described above. Data pertaining to the treatment and/or diagnosis may be communicated from the flow generator 104 to the computer terminal 106, e.g., via first and second wireless transmitters 108 and 110 respectively provided thereto.

The operator or sleep clinician may monitor the data and decide to adjust the course of treatment and/or diagnosis. Thus, in certain example embodiments, the operator or sleep clinician may be guided through different therapies and/or regimens via use the example application described above, running on the computer terminal 106. The operator or sleep clinician may be asked to input information pertaining to, for example, the therapy mode to be transitioned to, the particular treatment parameters of the current therapy mode and/or the therapy mode to be transitioned to, the way in which the transition is to be made (e.g., an immediate absolute change, partial changes in parameters that are discrete or substantially continuous, etc.), and/or other like information. In certain example embodiments, an operator or sleep clinician may be asked to confirm the transition and/or the particular settings related thereto, which may be recommended, user adjusted, and/or user specified. Control signals then may be relayed from the computer terminal 106 to the flow generator 104 via the second and first wireless communicators 110 and 108, respectively. These control signals may be received and interpreted by the flow generator 104. For example, a processor of the flow generator 104 may interpret the control signals received from the computer terminal 106 and adjust the treatment and/or diagnosis regimen appropriately.

It will be appreciated that updated data will be sent back to the computer terminal 106 from the flow generator 104, where it may be used and interpreted by the operator or sleep clinician and/or the application of certain example embodiments to manually, automatically, or semi-automatically inform decisions about how the treatment and/or diagnosis is proceeding and whether and how the next transition should be made. It also will be appreciated that the data and control signals also may be logged.

It will be appreciated that the data and/or control signals may be transmitted over a wired or wireless network such as, for example, the Internet, LAN, WAN, or other suitable network connections. Direct wired or wireless connections also may be used including, for example, Bluetooth connections, parallel or serial connections, etc. Advantageously, the connections may enable a patient and an operator or sleep clinician to be located remote from one another. Indeed, the patient may be located in a sleep clinic or even his or her own home, while an operator or sleep clinician may be located elsewhere in a sleep clinic or remote location, thereby further reducing the likelihood of the patient being disturbed, e.g., by human actions.

5. Example Methods for Guiding Transitions

Figure 12:
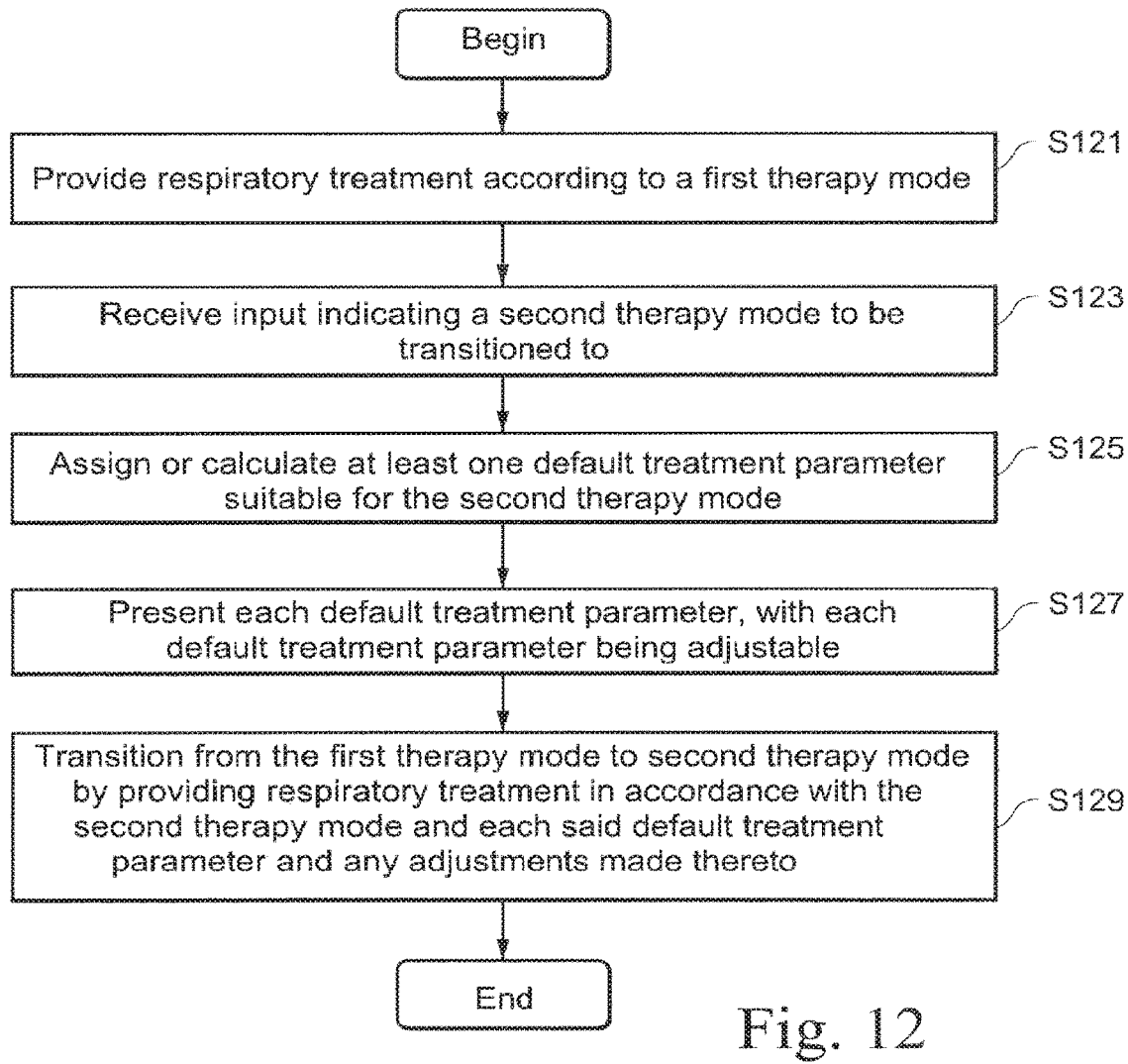
FIG. 12 is an illustrative flowchart showing a method for guiding transitions between therapy modes during the course of SDB treatment and/or diagnosis, in accordance with an example embodiment.

FIG. 12 is an illustrative flowchart showing a method for guiding transitions between therapy modes during the course of SDB treatment and/or diagnosis, in accordance with an example embodiment. In step S121, respiratory treatment is provided according to a first therapy mode. Input indicating a second therapy mode to be transitioned to is received in step S123. Prior to receiving such input, a recommendation as to the second therapy mode to be transitioned to may be generated, e.g., based on best practice guidelines or the like. In any case, at least one default treatment parameter suitable for the second therapy mode is assigned or calculated in step S125. Each default treatment parameter is presented to an operator or clinician, e.g., on a computer terminal display, on a flow generator, etc., in step S127. Additionally, an operator or clinician may adjust the default treatment parameters using an appropriate user interface, e.g., provided to the computer terminal, the flow generator, etc. A transition from the first therapy mode to the second therapy mode is performed by providing respiratory treatment in accordance with the second therapy mode and each said default treatment parameter and any adjustments made thereto in step S129. Such information may be conveyed in any suitable format. For example, all default treatment parameters, and any changes or "deltas" thereto may be conveyed in certain example embodiments. However, in certain example embodiments, only absolute treatment parameter values may be conveyed. Various other combinations and/or sub-combinations also are possible and are contemplated herein. The transitioning is performed in one step, e.g., so that all treatment parameters go into effect at substantially the same time. Additionally, in certain example embodiments, the transition may go into effect only after the operator or clinician has provided an appropriate confirmatory input.

Figure 13:
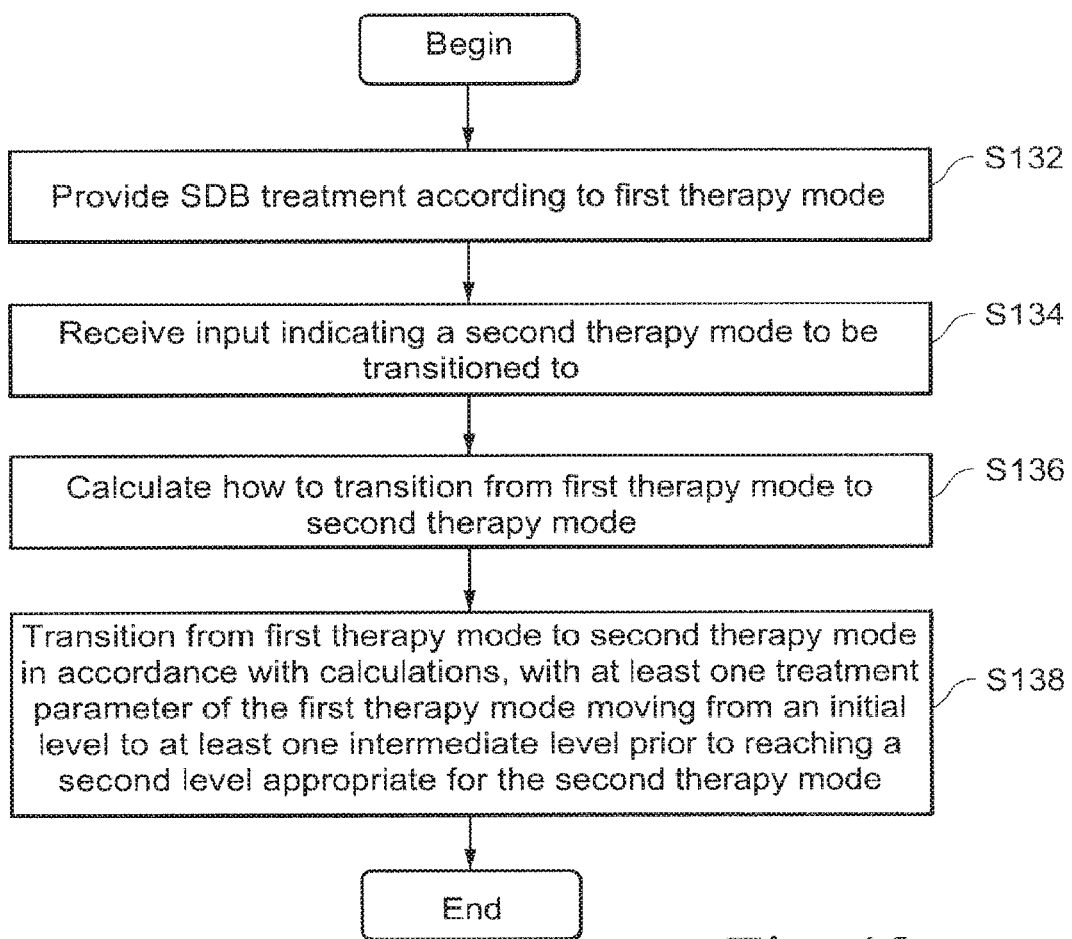
FIG. 13 is another illustrative flowchart showing a method for guiding transitions between therapy modes during the course of SDB treatment and/or diagnosis, in accordance with an example embodiment.

FIG. 13 is another illustrative flowchart showing a method for guiding transitions between therapy modes during the course of SDB treatment and/or diagnosis, in accordance with an example embodiment. In step S132, SDB treatment is provided according to a first therapy mode. Input indicating a second therapy mode to be transitioned to is received in step S134. Prior to receiving such input, a recommendation as to the second therapy mode to be transitioned to may be generated, e.g., based on best practice guidelines or the like. In any case, calculations are made regarding how the transition from the first therapy mode to the second therapy mode should be performed in step S136. These calculations may be refined by or based in whole or in part upon further user input. In step S138, a transition is made from the first therapy mode to the second therapy mode in accordance with the calculations. At least one treatment parameter of the first therapy mode moves from an initial level to at least one intermediate level prior to reaching a second level appropriate for the second therapy mode. Optionally, this process may continue, enabling transitions between additional modes.

As indicated above, the transition(s) from therapy mode to therapy mode may be controlled by an authorized user. When the user selects a particular therapy mode change, certain example embodiments may suggest appropriate therapy settings for the new mode. These new settings may be based on the current therapy settings in the current mode in certain example embodiments. The source of the proposed settings may come from a number of different sources, as indicated above. For example, the source of the proposed settings may be based on rules that the flow generator manufacturer has defined. However, in certain example embodiments, the source of the proposed settings may be based on rules that a sleep lab defines. Indeed, in certain example embodiments, a sleep lab may override or replace some or all pre-programmed proposed settings based on their own "default" values. This and other behaviors are described in greater detail below.

A flow generator manufacturer may sometimes ship its flow generators with "factory default values." Such factor default values sometimes may be defined in a shipping state matrix and loaded onto the device during manufacturing. Furthermore, different product codes (e.g., corresponding to different regions) sometimes may have different default values or even different ranges for a parameter. This may be advantageous, for example, to account for variations known to correlate well with different regions, etc. In certain example embodiments, a flow generator may be provided with a menu option to "restore defaults." This option may in certain example embodiments effectively "wipe" the current therapy settings and reapply the factory default values. In certain example embodiments, a sleep lab may be able to create its own set of default values. For example, the lab may prefer to always start with a CPAP of 6 cm $H_2O$. In such example embodiments, the device (and controller software) may allow the current therapy settings to be wiped and replaced with the lab defaults and/or the manufacturer's defaults. In so doing, a user may restore settings to the lab default prior to the start of a new titration (and, in the example above, start at that preferred CPAP of 6 cm $H_2O$). A sleep lab, in turn, may be encouraged to enter preferences for one or more therapy parameters in one or more modes or mode groupings.

For some mode transitions, the "new" mode being transitioned to may add therapy settings that have no "precedent" in the current mode. An example of this might be switching from simple CPAP mode to Spontaneous (S) mode. In this example, S mode adds the therapy setting Rise Time (how quickly the pressure transitions from expiratory to inspiratory pressure). Rise Time has no clear precedent in CPAP mode, at least insofar as the Rise Time setting does not exist in the CPAP mode and is not relevant to this therapy mode. In this scenario, it may sometimes be advantageous to make a sensible suggestion for Rise Time. This suggestion may be based on the Lab Default value for Rise Time in S mode. Thus, when a mode transition is made that involves a new setting that lacks a clear precedent in the current mode, a predefined manufacturer or sleep lab specified value may be referenced.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments.

Also, the various embodiments described above may be implemented in conjunction with other embodiments, e.g., aspects of one embodiment may be combined to provide treatment in connection with invasive ventilation techniques, volume modes, mechanical ventilation, etc. In addition, while the invention has particular application to patients who suffer from OSA, it is to be appreciated that patients who suffer from other illnesses (e.g., ventilatory insufficiency or failure, congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A method of guiding transitions between therapy modes in connection with the treatment and/or diagnosis of a patient for a respiratory disorder, the method comprising:
   providing respiratory disorder treatment to a mask using a flow generator according to a first therapy mode;
   receiving input in the flow generator from a response by an operator indicating a second therapy mode to be transitioned to following provision of the first therapy mode, said response being entered into a terminal and communicated to the flow generator, said input being received in the flow generator after the first therapy mode is initially provided, said second therapy mode being different from said first therapy mode;
   assigning or calculating at least one default treatment parameter using an application tangibly stored on a computer-readable storage medium accessible by the terminal, the at least one default treatment parameter suitable for the second therapy mode;
   presenting each said default treatment parameter of the second therapy mode to the operator using a display on the terminal, said presenting occurring after the first therapy mode is initially provided to the mask by the flow generator, each said default treatment parameter being adjustable by the operator during said presenting; and
   transitioning the flow generator from the first therapy mode to the second therapy mode by providing respiratory disorder treatment to the mask using the flow generator in accordance with the second therapy mode and each said default treatment parameter and any adjustments made thereto prior to said transitioning.

2. The method of claim 1, further comprising recommending the second therapy mode to be transitioned to and/or at least one said default treatment parameter of the second therapy mode prior to said receiving, said recommending being performed while the first therapy mode is being provided.

3. The method of claim 2, wherein said recommending is based on predefined rules.

4. The method of claim 3, wherein said predefined rules are updatable.

5. The method of claim 1, further comprising providing one or more further transition(s) between therapy modes.

6. The method of claim 5, wherein each further transition is provided according to a predefined progression.

7. The method of claim 1, wherein input is received in the flow generator from the terminal in a location remote from the patient.

8. The method of claim 7, wherein the input is received in the flow generator via wireless transmission from the terminal in the location remote from the patient.

9. The method of claim 1, wherein said transitioning is practiced by moving at least one treatment parameter of the first therapy mode provided by the flow generator from an initial level to at least one intermediate level prior to reaching a second level of a corresponding treatment parameter appropriate for the second therapy mode.

10. The method of claim 1, further comprising refining assignments or calculations of how to transition from the first therapy mode to the second therapy mode based on user input.

11. The method of claim 1, wherein said transitioning between said first and second modes involves moving at least one treatment parameter of the first therapy mode substantially continuously to a second level of a corresponding treatment parameter appropriate for the second therapy mode.

12. The method of claim 1, wherein the first and second therapy modes provided by the flow generator are selected from the group comprising: CPAP therapy mode, AutoSet therapy mode, VAUTO therapy mode, and S/ST/T therapy mode.

13. The method of claim 1, wherein a first pressure applied by the flow generator during the first therapy mode is a therapeutically effective pressure between 3-20 cm $H_2O$, and a second pressure applied by the flow generator during the second therapy mode is a therapeutically effective pressure between 3-20 cm $H_2O$.

14. The method of claim 1, wherein the input is received by the flow generator from the terminal via wireless transmission.

15. The method of claim 1, further comprising sensing a parameter associated with a patient's breathing cycle using a sensor on the flow generator, and transitioning from the first therapy mode to the second therapy mode after said parameter indicates an end of the patient's breath cycle, and prior to the patient beginning the immediately subsequent breath cycle.

16. The method of claim 1, wherein the first therapy mode is used to treat a first respiratory disorder and the second therapy mode is used to treat a second respiratory disorder different than the first respiratory disorder.

17. The method of claim 1, further comprising:
   generating a signal using the flow generator as a result of monitoring at least one of snoring sound, lack of breathing effort, progressiveness of increased apneas in the first therapy mode;
   recommending the second therapy mode to the operator using the terminal based on the signal; and receiving said input in the flow generator as the response to said recommending, said response being a confirmatory response.

18. The method of claim 1, further comprising:
generating a signal using the flow generator as a result of monitoring in the first therapy mode;
recommending the second therapy mode to the operator using the terminal based on the signal; and
receiving said input in the flow generator as the response to said recommending, said response being a confirmatory response.

19. The method of claim 1, further comprising assigning at least one constant treatment parameter used in the first therapy mode that is suitable for the second therapy mode;
presenting the at least one constant treatment parameter to the operator after the first therapy mode is initially provided; and
transitioning from the first therapy mode to the second therapy mode by providing respiratory disorder treatment in accordance with the second therapy mode and each said constant treatment parameter, wherein each said constant treatment parameter remains the same in the first therapy mode and in the second therapy mode.

20. The method of claim 1, wherein the input is received while the first therapy mode is being provided.

21. A system for guiding transitions between therapy modes provided to a patient suffering from a respiratory disorder, comprising:
a flow generator configured to supply a plurality of therapy modes to the patient, the flow generator being further configured to:
receive input indicating a second therapy mode to be transitioned to following provision of a first therapy mode, said input being received after the first therapy mode is initially provided, said input being a response by an operator that is communicated to the flow generator, said second therapy mode being different from said first therapy mode;
transition from the first therapy mode to the second therapy mode in accordance with instructions as to how to perform the transition, the instructions being indicative of at least one default treatment parameter suitable for the second therapy mode and any changes made by an operator to each said default treatment parameter after the first therapy mode is initially provided and prior to the transition.

22. The system of claim 21, wherein the flow generator is further configured to provide one or more further transition(s) between therapy modes.

23. The system of claim 22, wherein each said further transition is provided according to a predefined progression.

24. The system of claim 21, wherein said input is received from a location remote from the patient.

25. The system of claim 24, wherein said input is received at a computer terminal.

26. The system of claim 25, wherein an application tangibly stored on a computer-readable storage medium accessible by the computer terminal is configured to generate each said default treatment parameter included in the instructions as to how to perform the transition.

27. The system of claim 25, wherein the computer terminal is configured to display a recommendation as to the second therapy mode to be transitioned to and/or at least one said default treatment parameter of the second therapy mode.

28. The system of claim 24, wherein the flow generator is configured to be in a first room, and the location remote from the patient is configured to be in a second room different than the first room.

29. The system of claim 21, further comprising:
a display configured to display each said default treatment parameter; and
a user interface configured to receive said input from the operator indicative of changes to be made to said default treatment parameter prior to the transition.

30. The system of claim 21, wherein the transition is accomplished by adjusting at least one treatment parameter of the first therapy mode from an initial level to at least one intermediate level prior to reaching a second level of a corresponding treatment parameter appropriate for the second therapy mode.

31. The system of claim 21, wherein the flow generator is configured to supply a first therapeutically effective pressure between 3-20 cm $H_2O$ during the first therapy mode, and wherein the flow generator is configured to supply a second therapeutically effective pressure between 3-20 cm $H_2O$ during the second therapy mode.

32. The system of claim 21, further comprising a first wireless transmitter coupled to the flow generator and a second wireless transmitter remote from the flow generator, said input configured to be communicated wirelessly from the second wireless transmitter to the first wireless transmitter.

33. The system of claim 21, wherein transitioning is configured to occur between exhalation of one patient breath, and immediately subsequent inhalation of another patient breath in order to limit disturbances to the patient.

34. The system of claim 21, wherein the first therapy mode is configured to treat a first respiratory disorder and the second therapy mode is configured to treat a second respiratory disorder different than the first respiratory disorder.

35. The system of claim 21, wherein the flow generator is further configured to:
generate a signal as a result of monitoring at least one of snoring sound, lack of breathing effort, progressiveness of increased apneas in the first therapy mode;
recommend the second therapy mode based on the signal; and
receive said input as a confirmatory response to said recommendation.

36. The system of claim 21, wherein the flow generator is further configured to:
generate a signal as a result of monitoring in the first therapy mode;
recommend the second therapy mode based on the signal; and
receive said input as a confirmatory response to said recommendation.

37. The system of claim 21, wherein the instructions being indicative of at least one constant treatment parameter suitable for the second therapy mode that remains the same from the first therapy mode.

38. The system of claim 21, wherein the input is received while the first therapy mode is being provided.

* * * * *